United States Patent [19]

Nielsen

[11] Patent Number: 5,246,912
[45] Date of Patent: * Sep. 21, 1993

[54] HERBICIDAL COMPOSITIONS OF PHENMEDIPHAM AND DESMEDIPHAM

[75] Inventor: Erik Nielsen, Greve Strand, Denmark

[73] Assignee: Berol Nobel (Suisse) S.A., Switzerland

[*] Notice: The portion of the term of this patent subsequent to Aug. 30, 2005 has been disclaimed.

[21] Appl. No.: 776,868

[22] Filed: Oct. 16, 1991

Related U.S. Application Data

[63] Continuation of Ser. No. 198,306, May 25, 1988, abandoned, which is a continuation of Ser. No. 652,620, Sep. 20, 1984, Pat. No. 4,767,448.

[30] Foreign Application Priority Data

Feb. 29, 1984 [DK] Denmark .............................. 1486/84
Jun. 18, 1984 [DK] Denmark .............................. 2978/84

[51] Int. Cl.$^5$ .......................................... A01N 37/44
[52] U.S. Cl. ................... 504/135; 504/143; 504/301; 71/DIG. 1
[58] Field of Search .................. 71/111, DIG. 1; 504/135, 143, 301

[56] References Cited

U.S. PATENT DOCUMENTS

| | | | |
|---|---|---|---|
| 2,845,380 | 11/1953 | Mayhew et al. | 424/109 |
| 3,450,745 | 6/1969 | Payne, Jr. et al. | 560/28 |
| 3,535,101 | 10/1970 | Boroschewski et al. | 71/67 |
| 3,551,477 | 12/1970 | Koenig | 560/29 |
| 3,671,571 | 6/1972 | Koenig et al. | 560/29 |
| 3,692,820 | 9/1972 | Boroschewski et al. | 560/29 |
| 3,836,570 | 7/1974 | Szabo | 560/22 |
| 3,873,689 | 3/1975 | Frensch et al. | 424/78 |
| 3,933,460 | 1/1976 | Fischer | 71/88 |
| 3,992,188 | 11/1976 | Fischer | 71/92 |
| 3,997,322 | 12/1976 | Ratledge | 71/93 |
| 4,021,226 | 5/1977 | Preugschas et al. | 71/92 |
| 4,131,751 | 12/1978 | Koenig et al. | 560/29 |
| 4,188,202 | 2/1980 | Grillings et al. | 71/88 |
| 4,252,557 | 2/1981 | Boroschewski et al. | 71/100 |
| 4,452,630 | 6/1984 | Dal Moro et al. | 71/111 |
| 4,767,448 | 8/1988 | Nielsen | 71/111 |

FOREIGN PATENT DOCUMENTS 2237983 12/1982 Australia .
1669783 1/1984 Australia .
1669883 1/1984 Australia .

(List continued on next page.)

OTHER PUBLICATIONS

The Agrochemicals Handbook, Hartley et al., eds., p. A319 (a and b), Royal Society of Chem. (Oct. 1983).
Research Disclosure, "Improved Herbicide Treatment", No. 21725 (May 1982) p. 144–145.

Primary Examiner—Glennon H. Hollrah
Assistant Examiner—B. Beubenzk
Attorney, Agent, or Firm—Birch, Stewart, Kolasch & Birch

[57] ABSTRACT

Stabilized liquid herbicidal compositions containing at least one substituted phenyl carbamate of the general formula I

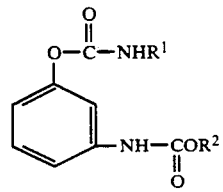

in which $R^1$ represents a $C_1$–$C_6$ alkyl group, a $C_3$–$C_6$ cycloalkyl group or an aryl group, which aryl group may be substituted by a halogen atom and/or a $C_1$–$C_6$ alkyl group and/or a trifluoromethyl group, and $R^2$ represents a $C_1$–$C_6$ alkyl, $C_2$–$C_6$ alkenyl or $C_2$–$C_6$ alkynyl group that may be substituted by a terminal halogen atom, and optionally at least one herbicidally active compound selected from the group consisting of 5-amino-4-chloro-2-phenyl-3(2H)pyridazinone, 2-ethoxy-2,3-dihydro-3,3-dimethylbenzofuran-5-yl methanesulphonate, and 4-amino-4,5-dihydro-3-methyl-6-phenyl-1,2,4-triazin-5-one are prepared by dispersing the compound(s) in finely ground state in a liquid phase which comprises one or more oily components and one or more surfactants and which is able to form an oil-in-water emulsion or a microemulsion when mixed with water.

15 Claims, No Drawings

FOREIGN PATENT DOCUMENTS

| | | |
|---|---|---|
| 131535 | 10/1970 | Denmark . |
| 102003 | 8/1983 | European Pat. Off. . |
| 0113857 | 12/1983 | European Pat. Off. . |
| 0197250 | 1/1986 | European Pat. Off. . |
| 2035158 | 1/1971 | Fed. Rep. of Germany . |
| 2341079 | 8/1973 | Fed. Rep. of Germany . |
| 66518 | 5/1983 | Finland . |
| 1127050 | 9/1968 | United Kingdom . |
| 1173753 | 12/1969 | United Kingdom . |
| 1193998 | 6/1970 | United Kingdom . |
| 1300094 | 12/1972 | United Kingdom . |
| 1358067 | 6/1974 | United Kingdom . |
| 1554595 | 10/1976 | United Kingdom . |
| 1482524 | 8/1977 | United Kingdom . |
| 2104519 | 3/1983 | United Kingdom . |
| 1123294 | 2/1984 | United Kingdom . |
| 2123294 | 2/1984 | United Kingdom . |

HERBICIDAL COMPOSITIONS OF PHENMEDIPHAM AND DESMEDIPHAM

This application is a continuation of application Ser. No. 07/198,306 filed on May 25, 1988, now abandoned, which was a continuation of Ser. No. 652,620 filed on Sep. 20, 1984 (U.S. Pat. No. 4,767,448).

FIELD OF THE INVENTION

The present invention relates to herbicidal compositions comprising phenyl carbamates and other herbicides.

TECHNICAL BACKGROUND

British patent specification No. 1,127,050 (claiming priority from German Patent Application No. Sch. 36854 IVb/12o dated Apr. 9th, 1965) (to Schering) discloses substituted phenylcarbamates of the general formula A

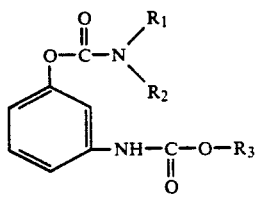

in which $R_1$ represents an alkyl group, a cycloalkyl group or an aryl group, which aryl group may be substituted by a halogen atom and/or an alkyl group and/or a trifluoromethyl group, $R_2$ represents a hydrogen atom or an alkyl group, or $R_1$ and $R_2$ together with the nitrogen atom may form a heterocyclic ring that may contain further nitrogen and/or oxygen atoms and $R_3$ represents an alkyl, alkenyl or alkynyl group that may be substituted by a terminal halogen atom, which compounds are useful for selectively combating weeds in crop areas. The herbicidal activity is observed in both pre-emergence and post-emergence treatments, thus allowing preparations containing said compounds A to be applied by whichever method is desired. The herbicidal activity is also observed when compounds A are applied on the leaves of established weeds, and the compounds are especially useful in combating weeds in beet fields, especially as post-emergence herbicides in sugar beet fields.

An especially preferred compound of the general formula A is methyl (3-(3-tolyl-carbamoyloxy)phenyl)-carbamate which has later been given the common name phenmedipham. Another especially preferred compound is ethyl (3-phenyl-carbamoyloxyphenyl)carbamate which has later been given the common name desmedipham. Methyl (3-(3-tolyl-carbamoyloxy)-phenyl)carbamate is commercially available under the trade mark Betanal and is used especially as post-emergence herbicide for the weeding of beet crops, in particular sugar beet, at an application rate of 1 kg a.i./2-00-300 liters/ha. It has been reported (*Pesticide Manual, A World Compendium*, The British Crop Protection Council, 6th Edition, 1979) that the compound acts through the leaves with little action via the soil and roots. In the soil there was, in three months, a 71–86% degradation of the a.i. (active ingredient) detected one day after treatment.

According to the British patent specification, compounds A may be prepared, e.g., by the following processes:

When $R_2$ represents a hydrogen atom, by reacting N-hydroxyphenyl carbamates of the general formula

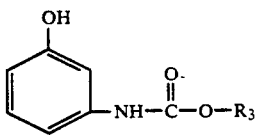

with a) isocyanates of the general formula $$R_1-N=C=O$$

in the presence of a catalyst, suitably an organic base, preferably triethylamine, or with b) carbamic acid chlorides of the general formula

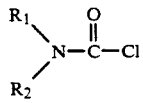

in the presence of an acid acceptor, suitably an inorganic or organic base, preferably pyridine, or, when $R_2$ represents alkyl, or is a member of a heterocyclic ring, the indicated N-hydroxyphenyl carbamates are reacted as indicated with the indicated carbamic acid chlorides, $R_1$ and $R_3$ in the above formulae having the definitions given above and $R_2$ having the corresponding definition in each case.

According to the above-mentioned British patent specification, both reaction a) and reaction b) are carried out in organic solvents such as tetrahydrofuran or anhydrous pyridine in order to avoid the influence of water on the isocyanate.

British Patent No. 1,173,753 (to Schering) discloses herbicidally active compounds having a formula closely related to formula A above, i.e., compounds of the general formula B

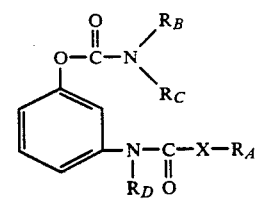

in which $R_A$ represents an alkyl or alkenyl group of at the most 5 carbon atoms, an alkynyl group of 3 or 4 carbon atoms, a cycloalkyl group of 3–6 carbon atoms, a phenyl group, a benzyl group or a methoxyethyl group, $R_B$ represents an alkyl group of 1–8 carbon atoms, an alkenyl group of 2–4 carbon atoms, a cycloalkyl group of 3–6 carbon atoms, an optionally by halogen substituted phenyl group, a methoxyphenyl group, a methylphenyl group or a chloroethyl group, $R_C$ represents hydrogen or an alkyl group of 1–3 carbon atoms, or $R_B$ and $R_C$ together with the nitrogen atom to which they are attached form a piperidino group, and $R_D$ represents hydrogen or methyl, and X represents oxygen or sulphur, except compounds used as active components in the herbicidal preparation according to British Patent No. 1,127,050.

According to the examples in British Patent Specification No. 1,173,753, the preparation of the 3-(carbamoyloxy)carbanilates is performed in organic solvents such as ether, ethyl acetate, benzene, etc.

Tetrahydrofuran, pyridine and many other organic solvents are known to be hazardous to the health. The use of organic solvents demands separation thereof from the effluents, and from an economical point of view it is necessary to re-use organic solvents.

The above-mentioned British patent specification No. 1,127,050 also discloses that the N-hydroxyphenyl carbamates required as starting products may be prepared by N-acylation of 3-aminophenol with the appropriate chloroformic acid esters, for example, in a mixture of ethyl acetate and water in the presence of magnesium oxide. The effect of ethyl acetate is to dissolve the carbamate as it is formed, and the water dissolves the magnesium chloride formed. 3-Aminophenol is not dissolved by ethyl acetate, and the reaction medium thus contains 3-aminophenol and magnesium oxide suspended therein. Excess magnesium oxide can be dissolved in dilute HCl, thus yielding two liquid phases. The isolation and purification of the product is rather complicated due to the character of the two-phase medium, the organic medium comprising the N-hydroxyphenyl carbamate dissolved therein. The phases are separated, and the organic phase is washed neutral with water and then with dilute potassium bicarbonate solution. After drying and evaporation of the organic phase, the crude product is redissolved in ether and precipitated with light petroleum. The yield of the N-hydroxyphenyl carbamate is stated to be 83%, based on the starting material 3-aminophenol. The loss is probably due to the loss of 3-aminophenol in the form of hydrochloride. Due to the contents of $MgCl_2$, the aqueous phase cannot be used in the next batch and hence, it is necessary to extract 3-aminophenol which, however, is only slightly soluble in common organic water-immiscible solvents. Hence, the known methods for the preparation of the starting materials are disadvantageous from an economic point of view as a loss of starting material of 17% is unsatisfying, and the isolation and purification is complicated, and the process for the preparation of the end products, the substituted phenyl carbamates, is disadvantageous in being carried out in solvents which are hazardous to the health.

BRIEF DESCRIPTION OF THE INVENTION

It has now been found that the preparation of a valuable class of herbicidally active substituted phenyl carbamates which are encompassed by the general formula A above can be performed in an aqueous medium, giving a high yield with excellent purity.

From an environmental point of view it is of course desirable to carry out chemical reactions in non-toxic solvents and it is always most desirable to carry out the reactions in aqueous media.

Accordingly, the present invention relates to a process for the preparation of substituted phenyl carbamates of the general formula I

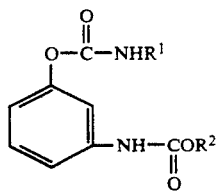

in which $R^1$ represents a $C_1$–$C_6$ alkyl group, a $C_3$–$C_6$ cycloalkyl group or an aryl group, which aryl group may be substituted by a halogen atom and/or a $C_1$–$C_6$ alkyl group and/or a trifluoromethyl group, and $R^2$ represents a $C_1$–$C_6$ alkyl, $C_2$–$C_6$ alkenyl or $C_2$–$C_6$ alkynyl group that may be substituted by a terminal halogen atom, by reaction of N-hydroxyphenyl carbamates of the general formula II

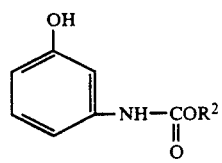

wherein $R^2$ is as defined above, with either
i) isocyanates of the general formula IV

$$R^1-N=C=O \qquad IV$$

or
ii) carbamic acid chlorides of the general formula V

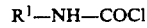

$$R^1-NH-COCl \qquad V$$

wherein $R^1$ is as defined above, which process is characterized in that both of the reactions i) and ii) are performed in an aqueous medium. The preparation of the N-hydroxyphenyl carbamates II can be performed in an aqueous medium also.

It has also been found that the substituted phenyl carbamates and other herbicides may be particularly advantageously formulated in oil-containing compositions such as described in greater detail in the following.

DETAILED DESCRIPTION OF THE INVENTION

The term "$C_1$–$C_6$ alkyl group" designates straight and branched aliphatic hydrocarbon radicals containing 1 to 6 carbon atoms such as methyl, ethyl, propyl, isopropyl, butyl, isobutyl, tert.butyl, sec.butyl, pentyl and 1-ethylpropyl. The term "$C_2$–$C_6$ alkenyl group" designates straight and branched aliphatic hydrocarbon radicals containing 2 to 6 carbon atoms and comprising a double bond such as allyl, 2-methylallyl and 2-butenyl. Similarly, the term "$C_2$–$C_6$ alkynyl group designates straight and branched aliphatic hydrocarbon radicals containing 2 to 6 carbon atoms and comprising a triple bond such as propynyl and 1-methyl-2-propynyl. The term "$C_3$–$C_6$ cycloalkyl group" designates saturated cyclic hydrocarbon radicals containing 3 to 6 carbon atoms such as cyclopropyl and cyclohexyl, etc.

The term "aryl" preferably designates phenyl, and a preferred substituent on the aryl group is a $C_1$–$C_6$ alkyl group as defined above, in particular methyl, in the meta-position. The term "halogen" designates fluorine, chlorine, bromine and iodine.

The term "aqueous medium" designates media in which at least 50%, preferably at least 90% and most preferably 100%, of the solvent is water.

When the medium is a mixture comprising water, the other liquid components therein may be water-miscible or water-immiscible solvents selected from the group of solvents which do not react with the starting materials such as acetone, benzene or xylene.

It is especially preferred to perform the process in substantially 100% of water, i.e., substantially without any other liquid components present.

In the reaction of N-hydroxyphenyl carbamates II and isocyanates IV or carbamic acid chlorides V, pH in the aqueous medium should be an alkaline pH, that is at least pH 8, in order to promote formation of the anion of the compound II as it is the anion which is able to react with the isocyanate IV or the carbamic acid chloride V. pH in the reaction medium should, however, be at the most 10. The most preferred pH in an aqueous medium is about 9. The alkaline pH may be maintained during the process by adding base, e.g. by the use of a pH-stat. The medium may also be kept in the desired range of 8-10 by means of an adder buffer. At the end of the reaction, it may be necessary to add an acid in order to keep the pH in the range of 8-10.

When the pH in the reaction medium is kept in the desired range of 8-10 by addition of a base, the base may be any suitable organic or inorganic base such as a tertiary amine, e.g. triethylamine, an alkali metal hydroxide such as sodium hydroxide, etc. If an acid is to be added, a mineral acid such as HCl is preferred.

In the reaction medium, a side reaction may occur, i.e. a reaction between water and isocyanate yielding N,N'-di-($R^1$)-urea according to the following equation:

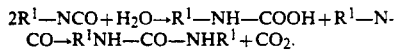

$$2R^1\text{—}NCO + H_2O \rightarrow R^1\text{—}NH\text{—}COOH + R^1\text{—}N\text{-}CO \rightarrow R^1NH\text{—}CO\text{—}NHR^1 + CO_2.$$

The carbamic acid chlorides give rise to a similar side reaction as they in a first step are converted into isocyanates which then react with water as indicated above.

In order to suppress the loss of isocyanate or carbamic acid chloride due to the side reaction, the isocyanate IV or the carbamic acid chloride V should be used in an amount of at the most equimolar in relation to the carbamate; it is preferred that the molar ratio of the carbamate to the isocyanate is in the range of 2:1 to 1:1.

Furthermore, it is possible to suppress the loss of isocyanate or carbamic acid chloride by adding them to the medium comprising the carbamate at the rate at which they react.

The isocyanate or carbamic acid chloride should be added to the reaction medium containing the N-hydroxyphenyl carbamate under vigorous stirring or agitation in order to accelerate the contact between the isocyanate or the carbamic acid chloride and the N-hydroxyphenyl carbamate and, hence, to prevent the side reaction between isocyanate or carbamic acid chloride and water. On an industrial scale, vigorous stirring or agitation may be achieved e.g. by means of an impeller, and furthermore the contents of the reaction vessel may be agitated by circulation in a circulation pipe by means of a circulating pump. It is especially advantageous to supply the isocyanate or the carbamic acid chloride into a circulation pipe, e.g. by means of a nozzle, thereby obtaining an intimate contact between droplets of the isocyanate or the carbamic acid chloride and the carbamate intermediate in the aqueous medium.

As the medium in which the reaction is performed mainly consists of water, a suitable reaction temperature is 0°-100° C. It is believed that a low temperature suppresses the formation of by-products, and hence, the reaction should be carried out at 10°-30° C., preferably at 10°-20° C.

The amount of reactants in the aqueous medium should preferably be kept at 0.1-2 moles of each of the reactants per liter aqueous medium, the upper limit requiring very vigorous agitation.

The solubility of the product I is considerably lower than that of the intermediate II thus giving the risk of having particles of intermediate II "trapped" in particles of I. The "trapping" of II seems to be minimized by using more diluted reaction mixtures. If reactants II and IV or V are reacted in equimolar amounts, it is preferred to carry out the reaction at a concentration of 0.1-0.4 moles/liter of each of the reactants, preferably at about 0.1-0.3 moles/liter, more preferably at about 0.2-0.3 moles/liter, especially at about 0.25-0.30 moles/liter.

It is preferred to react a slurry of the phenyl carbamate intermediate in which the liquid phase consists of a saturated solution of the phenyl carbamate intermediate, with the isocyanate or the carbamic acid chloride, the amount of isocyanate or carbamic acid chloride added being less than the stoichiometric amount. During the reaction in which dissolved phenyl carbamate intermediate is removed as reaction product, further amounts of phenyl carbamate dissolve.

After the completion of the reaction, the reaction product, which is very heavily soluble in water, may either be isolated and purified in a conventional manner, e.g., by filtration and washing with water followed by drying, or be removed from the aqueous phase by extraction with an organic solvent (or solvent mixture) which is substantially water-immiscible or miscible with water to only a minor extent.

Solvent extraction is a preferred method of isolating the desired end product as solvent extraction equipment is less expensive than filtering and drying equipment.

Normally, a drying process leads to a slight degradation of the end product, and therefore, omission of the drying step is advantageous.

Suitably, the extracting solvent (or solvent mixture) is the same solvent (or solvent mixture) which is used in the later formulation of commercial liquid compositions containing the compounds I, for example ketones such as isophorone. In order to facilitate the separation of the solvent phase and the aqueous phase it may be advantageous to add a density-increasing agent to the aqueous phase, e.g. sodium chloride. As the end product I is more stable at acidic conditions, it is preferred to adjust the pH in the reaction medium on an acidic pH before the addition of the organic extraction solvent, or the solution of I in the organic solvent (or solvent mixture) may be washed with water at acidic pH (e.g. about 2) and containing a density-increasing agent such as sodium chloride.

The phase separation may be carried out by centrifugation or by simple gravity separation. After the phase separation the organic solution of compound I may then be used in the formulation of compositions. The organic phase may, if necessary, be dried with a dessicant, e.g. $Na_2SO_4$.

After the preparation, the end product dissolved in the extraction solvent may be formulated directly into liquid concentrates in a very simple manner as all of the components for the formulation of the liquid composition are then in liquid form.

The process of the invention has several advantages over the above-mentioned prior art, viz:

i) no organic solvents are to be handled;

ii) the process is more simple as the resulting product is simply isolated by filtration, which means that additional precipitation is avoided, or the resulting product is removed by solvent-extraction as explained above.

According to Houben-Weyl, Methoden der organischen Chemie, p. 129, Vol. 8, 4th Edition, 1952, isocyanates react readily with compounds containing a reactive hydrogen atom, e.g. water, alcohols, phenols and amines. Indeed, isocyanate reacts so vigorously with water that a quantitative method for the determination of water by means of isocyanates has been developed (*Journal of Chromatography* 178, 1979, pp. 271-276: "Sensitive high-performance liquid chromatographic method for the determination of water in various samples"). The method is based on the formation of diaryl urea according to the following equation $$2R^1-NCO+H_2O \rightarrow R^1-NH-COOH+R^1-N-CO \rightarrow R^1NH-CO-NHR^1+CO_2.$$

It was therefore surprising that the reaction between the isocyanate and the N-hydroxyphenyl carbamate in the process of the invention proceeds preferentially to the reaction between isocyanate and water with excellent yields and with the other advantages mentioned above.

According to the invention, it is preferred to prepare compounds of the general formula I in which $R^1$ represents a phenyl group which is optionally substituted, suitably in m-position, by a $C_1$–$C_6$ alkyl group, preferably a methyl or ethyl group, and $R^2$ represents a $C_1$–$C_6$ alkyl group, preferably a methyl or ethyl group, by reaction of corresponding N-hydroxyphenyl carbamates II with corresponding isocyanates IV or carbamic acid chlorides V, in an aqueous medium, preferably in water.

A preferred embodiment of the invention is a process wherein methyl N-(3-hydroxyphenyl)carbamate is reacted in water with 3-tolyl isocyanate to yield methyl (3-(3-tolyl-carbamoyloxy)phenyl)carbamate, and a process wherein ethyl N-(3-hydroxyphenyl)carbamate is reacted in water with phenyl isocyanate to yield ethyl (3-phenyl-carbamoyloxyphenyl)carbamate. Another preferred embodiment of the invention is a process wherein methyl N-(3-hydroxyphenyl)carbamate is reacted in water with 3-tolyl carbamic acid chloride to yield methyl (3-(3-tolyl-carbamoyloxy)phenyl)carbamate, and a process wherein ethyl N-(3-hydroxyphenyl)carbamate is reacted in water with phenyl carbamic acid chloride to yield ethyl (3-phenyl-carbamoyloxyphenyl)carbamate.

Normally, the process involving the use of the isocyanate is preferred to the process involving the carbamic acid chloride due to the instability of the carbamic acid chloride.

In one aspect of the invention, the N-hydroxyphenyl carbamates of the general formula II used as starting materials are prepared by reaction of 3-aminophenol with a chloroformate of the general formula III

   III wherein $R^2$ is as defined above, which process is performed in an aqueous medium in the presence of an acid receptor.

In this reaction, the carbamate is formed with simultaneous liberation of HCl. If the HCl is not removed, it will react with the amino group in 3-aminophenol and inactivate the amino group. Therefore, an acid receptor is required. According to the invention, the acid receptor is preferably a water-soluble base. The water-soluble base may be an organic base such as pyridine or an inorganic base such as alkali metal hydroxides, carbonates and hydrocarbonates, alkali metal phosphates and borates such as sodium hydroxide, sodium carbonate, disodium hydrogen phosphate, borax, etc. An especially preferred water-soluble base is sodium hydroxide.

The aqueous medium comprises at least 70%, preferably at least 90%, most preferably 100% of water.

When the solvent is a mixture comprising water, the other liquid components therein may be water-miscible or water-immiscible solvents selected from the group of solvents which do not react with the starting materials such as acetone, benzene or xylene.

The process for the preparation of the N-hydroxyphenyl carbamate is preferably performed at pH 2-7, most preferably at pH 4.3-6.3, more preferably at pH 5-6, especially at pH 5-5.5, e.g. about pH 5.3.

If the pH is high, i.e. above about 7, a side reaction comprising reaction of the chloroformate III with the hydroxy group in the 3-aminophenol may occur. Said reaction does not take place, at least not to a significant extent, if the reaction medium comprises unreacted amino groups and is acidic. In a preferred embodiment of this process, the chloroformate is added to the aqueous medium comprising the 3-aminophenol at the rate at which it is reacted. It is possible to carry out the reaction using a large molar excess of 3-aminophenol, but this implies the necessity of recovering large amounts of 3-aminophenol after completion of the reaction. It is preferred that the molar ratio of 3-aminophenol to chloroformate is 2:1–1:1, especially 1:1.

It is preferred to adjust the pH in the starting solution of 3-aminophenol to about 5-5.5 such as 5.3 before the addition of chloroformate III in order to avoid an initial reaction with the hydroxy group in the 3-aminophenol. Said pH-adjustment may be performed by means of e.g. HCl.

The amount of reactants in the aqueous medium is suitably at the most 1 mole per liter, preferably about 0.5 moles per liter.

The reaction temperature is suitably below 50° C., preferably below 25° C., especially 0°-15° C., advantageously at about 10° C. The reaction mixture may be cooled by supplying ice directly into the reaction vessel.

After the reaction between 3-aminophenol and the chloroformate, the pH in the medium may be lowered to less than 3, especially less than 2, in order to dissolve remaining parts of the aminophenol in the aqueous phase as an acid addition salt thereof, preferably by means of hydrochloric acid, said removal of aminophenol being desirable if aminophenol has been used in a molar excess.

After isolation of the N-hydroxyphenyl carbamates II and washing thereof with water, the mother liquor plus the washings may be used as part of the reaction medium for the next batch.

A preferred compound of formula II, methyl N-(3-hydroxyphenyl)carbamate, can be transferred to the next reaction stage in melted form as it may be melted at 50°-55° C. when covered with the aqueous washing phase as it has been found that, when covered with water, the product melts at a lower temperature than the melting point of the crystalline material. This yields a two-phase system, the lower oily phase being the carbamate in liquid form, and the upper phase being the aqueous phase containing unreacted 3-aminophenol in the form of its acid addition salt. After separation of the phases, the oily product may be washed by agitation with water, and after renewed separation of the phases the phenyl carbamate intermediate may be used in the next reaction step.

This preferred aspect of the invention in which the starting material is prepared in aqueous solution has several advantages over the prior art, i.e.

i) liberated HCl is neutralized as non-toxic NaCl by the unexpensive product sodium hydroxide;

ii) the yield of the process is high, i.e. at least about 95% and often substantially 100%, thus reducing the amount of 3-aminophenol to be recovered;

iii) process equipment is less expensive as no organic solvents have to be handled, and the process per se is simple;

iv) the product may be melted when covered with water and is consequently easy to purify by washing with water and to pump to the next stage in the reaction.

A preferred aspect of the invention is directed to a two-stage synthesis process for the preparation of substituted phenyl carbamates of the general formula I above, which process is characterized in that A) 3-aminophenol is reacted with a chloroformate of the general formula III

 ClCOOR$^2$  III wherein R$^2$ is as defined above, in an aqueous medium;

B) the product of the general formula II

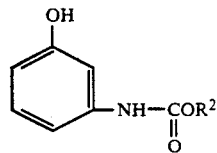  II wherein R$^2$ is as defined above, is isolated; and

C) the product of the general formula II is reacted with either i) isocyanates of the general formula IV

 R$^1$—N=C=O  IV or ii) carbamic acid chlorides of the general formula V

 R$^1$—NH—COCl  V wherein R$^1$ is as defined above, in an aqueous medium.

In an especially preferred embodiment of the invention, methyl (3-(3-tolyl-carbamoyloxy)phenyl)carbamate is prepared by A′) reacting 3-aminophenol with methyl chloroformate in an aqueous medium, B′) isolating the methyl N-(3-hydroxyphenyl)carbamate, and C′) reacting the isolated carbamate with either
i) 3-tolyl isocyanate or
ii) 3-tolyl carbamic acid chloride in an aqueous medium.

In another especially preferred embodiment of the invention, ethyl 3-phenyl-carbamoyloxyphenyl carbamate is prepared by A″) reacting 3-aminophenol with ethyl chloroformate in an aqueous medium, B″) isolating the ethyl N-(3-hydroxyphenyl)carbamate, and C″) reacting the isolated carbamate with either
i) phenyl isocyanate or
ii) phenyl carbamic acid chloride in an aqueous medium.

Another preferred aspect of the invention is directed to a one-pot synthesis process for the preparation of the substituted phenyl carbamates of the general formula I above, which process is characterized in that step A and thereafter step C as explained above are performed in one reaction vessel, thus leaving out step B. In the preferred embodiments as indicated above, the steps B′ and B″ are, therefore, omitted.

Hence, compounds of the formula I as defined above may be prepared by a process which is characterized in that 1) 3-aminophenol is reacted with chloroformate of the general formula III

 ClCOOR$^2$  III wherein R$^2$ is as defined above, in a molar ratio of about 1:1, in aqueous medium, and 2) the resulting product is reacted in situ, without isolation, with either i) isocyanates of the general formula IV

 R$^1$—N=C=O  IV or ii) carbamic acid chlorides of the general formula V

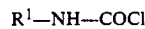 R$^1$—NH—COCl  V wherein R$^1$ is as defined above, in a molar ratio of about 1:1, in an aqueous medium, the process steps 1) and 2) being carried out as subsequent steps in the same reaction vessel.

This one-pot synthesis is performed in such a manner that substantially equimolar amounts of 3-aminophenol and the chloroformate of the general formula III are reacted in an aqueous medium, the pH being adjusted to the range of 2-7, preferably 4.3-6.3, more preferably 5-6, especially 5-5.5, e.g. 5.3 by preliminary addition of an acid and simultaneous addition of a base solution. When the pH is lowered to about 5-5.5, e.g. to about 5.3, before the addition of the chloroformate, no side reaction with the hydroxy group occurs. Hence, it is possible to use a slight excess of chloroformate in order to make sure that all the 3-aminophenol is reacted. The excess of chloroformate, if any, will be decomposed in the next reaction step. Preferably a minor excess of chloroformate is used, the molar ratio of 3-aminophenol to chloroformate being 1:1-1.5, preferably 1:1-1.1, most preferably 1:1.01-1:1.05. When the reaction is complete, pH is increased to above 7, preferably to above 8 and more preferably to about 9.2 by addition of a further amount of a base solution. The resulting product is reacted in situ with the isocyanate or the carbamic acid chloride which is added dropwise for the formation of the desired substituted phenyl carbamate I. In the second reaction step, equimolar amounts of reactants are reacted. In a preferred embodiment, cooling is performed by adding ice to the reaction vessel during step 1, which also leads to an advantageous dilution of the reaction mixture for step 2. In a further preferred embodiment, seed crystals of the desired end product are added to the reaction vessel before the addition of the isocyanate or the carbamic acid chloride in step 2, thus facilitating the crystallization of the end product.

In another preferred embodiment the reaction slurry obtained in step 2 is subjected to extraction with a solvent (or solvent mixture) as explained above.

In an especially preferred embodiment of this aspect of the invention, methyl (3-(3-tolyl-carbamoyloxy)-phenyl)carbamate is prepared by reacting equimolar amounts of 3-aminophenol with
  methyl chloroformate in water, the temperature being maintained at about 10° C. by addition of ice and pH being maintained in the range of 4.3–6.3, preferably 5–6, especially 5–5.5, e.g. to about 5.3, by addition of a base solution, adjusting pH to an alkaline value by addition of further base solution, and
reacting the methyl N-(3-hydroxyphenyl)carbamate formed in situ with either
  i) 3-tolyl isocyanate or
  ii) 3-tolyl carbamic acid chloride
in the same reaction vessel.

It is especially preferred to carry out the reaction in the second step at a concentration of about 0.1–0.4 moles/liter, preferably at about 0.2–0.3 moles/liter and more preferably at about 0.25–0.3 moles/liter.

The resulting slurry is preferably subjected to solvent extraction with a water-immiscible solvent in which methyl (3-(3-tolyl-carbamoyloxy)phenyl)carbamate is soluble.

The substituted phenyl carbamates prepared according to the invention may be used either alone or in admixture with one another and/or other herbicides and/or other substances, for example fertilizers, for combating weeds.

They may be used in the form of concentrated compositions for dilution with water at the site of use, the compositions, e.g., being of the types commonly used for combating weeds, for example wettable powders or dispersions, using liquid and/or solid carriers or diluents and dispersing agents and surfactants.

The compositions may be made by methods normally used for the preparation of such herbicidal compositions.

Suitable liquid diluents are, for example, organic solvents such as cyclohexanone, isophorone, decalin, tetralin, dimethylformamide and dimethylsulphoxide, and mixtures thereof.

Suitable solid carriers are, for example, kaolin, talc, natural or synthetic silicic acid, attapulgite and other clays.

Suitable surfactants are, for example, salts of lignosulphonic acid, salts of alkylated benzenesulphonic acids, polyethoxylated amines, polyethoxylated alcohols and polyethoxylated phenols.

In the formulation of commercial liquid herbicidal concentrates of substituted phenyl carbamates I, it is customary to include a solvent which is capable of dissolving the phenyl carbamate I and which facilitates later dilution of the composition on the location in which the composition is to be used. As already indicated above, isophorone is normally used as the solvent in the formulation of such compositions, as isophorone is a fairly good solvent for the phenyl carbamates I and the phenyl carbamates I are chemically relatively stable in solution in isophorone, in particular when the phenyl carbamates I have been washed or treated with acid at a pH of about 2–4 prior to dissolving them in isophorone. Another advantage of the use of isophorone is that it is only slightly soluble in water (if a water-soluble solvent were used in the concentrate, it would tend to dissolve in the aqueous phase when the liquid preparation ready for application is prepared on location by addition of water, which would cause the phenyl carbamate to precipitate with a consequent decrease in its biological activity and blocking of the spraying equipment).

It is customary to include ionic emulsifiers such as calcium dodecyl benzene sulfonate in commercial solutions of phenmedipham in isophorone. It has also been suggested to use salts of phosphoric acid esters as emulsifiers. In accordance with an aspect of the present invention, it has been found that ampholytes are interesting and useful emulsifiers for solutions of phenmedipham in isophorone, preferably in combination with non-ionic surfactants. It is assumed that the ionic character of ampholytes counteracts the tendency which phenmedipham otherwise has to precipitate, first as an oil and later as microcrystals, when the composition is mixed with water for preparing the solution ready for use. It is believed that the function of the ampholyte is to act as emulsifiers and dispersing agents for any precipitated active substance in the oily state so that precipitation of solid is delayed or avoided.

As examples of ampholytes which are useful in solutions of phenmedipham in isophorone may be mentioned N-alkyl-β-aminopropionic acids (wherein alkyl designates groups of 8–22 carbon atoms), N-alkyl N-dimethylamino acetic acid (betaine) and imidazolin-amphotensides such as compounds of the formulae

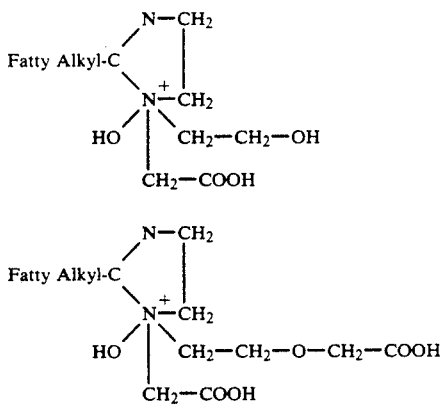

and carboxymethylated and ethylated derivatives of the formulae

Carboxymethylated derivatives:

Monocarboxylic acid

-continued

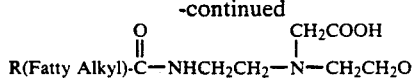

Dicarboxylic acid

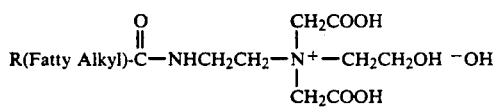

Carboxyethylated derivatives:

Monocarboxylic acid

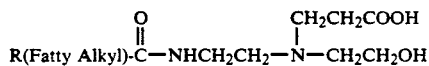

Dicarboxylic acid

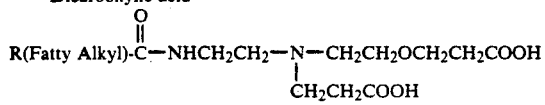

wherein Fatty Alkyl is $C_{8-22}$ alkyl.

Normally, the concentrated solutions of phenmedipham in isophorone have a concentration of phenmedipham in the range of 10-20%. When one or several ampholytes are used as emulsifiers in the solutions, the ampholyte or ampholytes is/are normally present in an amount of 1-20%, preferably 2-12%, more preferably 3-7% by weight, calculated on the weight of the composition. A preferred ampholyte for use in this aspect of the invention is coco alkyl-$\beta$-amino propionic acid which is preferably present in an amount of 2-10%, preferably 3-7%, e.g. about 5% by weight of the composition.

One advantage of the use of ampholytes as emulsifiers in solutions of phenyl carbamates I in isophorone is that ampholytes are compatible with all types of emulsifiers, both anionic, cationic and non-ionic and, at the same time, are good emulsifiers for solids, and therefore they will in general be very useful when the composition is made up with water for the preparation of solutions ready for use together with, e.g., pesticides and other herbicides. As examples of other herbicides, 5-amino-4-chloro-2-phenylpyridazin-3-one, 2-ethoxy-2,3-dihydro-3,3-dimethylbenzofuran-5-yl methanesulphonate, and 4-amino-4,5-dihydro-3-methyl-6-phenyl-1,2,4-triazin-5-one may be mentioned.

As an interesting alternative to the solutions of the phenyl carbamates I in isophorone, it has been found, according to an aspect of the invention, that the biological activity of substituted phenyl carbamates I is advantageously high when the phenyl carbamates are "activated" by being presented in the form of suspensions of the compounds in finely ground state in liquid phases comprising one or several oily components and one or several surfactants, the liquid phase being able to form an oil-in-water emulsion or a microemulsion when mixed with water at the site of use for making the final preparation ready for use. The oily component is suitably a water-insoluble substance selected from the group consisting of mineral oils, vegetable oils, liquid synthetic lower carboxylic acid esters of monoalcohols or of dihydric, trihydric or other lower (e.g. 4-6 hydroxy functions) polyalcohols, chlorinated oils, ethers, water-insoluble alcohols, ketones and polyglycols, and mixtures thereof. As examples of mineral oils may be mentioned spindle oil, aromatic compounds such as propylbenzene and dodecylbenzene, parafinic oils, etc.; as examples of vegetable oils may be mentioned soy oil, rape seed oil, olive oil, etc.; as examples of liquid esters of alcohols may be mentioned 2-ethylhexyl stearate and 2-ethyl-hexyl adipate, etc.; as examples of chlorinated oils may be mentioned chlorinated $C_{10}$-$C_{24}$ hydrocarbons and chlorinated aromatics; as examples of ethers may be mentioned octyl phenyl ether, etc.; as an example of alcohols may be mentioned decanol; and as examples of water-insoluble polyglycols may be mentioned polypropylene glycol, optionally substituted by polyethylene glycol, etc. Oily components are furthermore compounds which fulfil each of the conditions that they should be liquid at normal temperatures, be immiscible with water in a ratio of 1:10-10:1 by weight, comprise at least 67% by weight of hydrocarbyl or hydrocarbylene and optionally halogen, calculated on the total chemical composition thereof, and be one in which the solubility of the substituted phenyl carbamates I is less than 1% by weight. (Polypropylene glycol which is a preferred oily substance, has the formula $HO(CH_2—CH_2CH_2O)_nH$. When n is a large number, the content of hydrocarbylene in the polypropylene glycol is $$\frac{3 \times 14}{3 \times 14 + 16} \times 100 = 72.4\%.)$$

The suspensions of the phenyl carbamates I in oily components and surfactants may have an oil content of oily substance of 5-75%, in particular about 15-65%, by weight, calculated on the composition. The surfactant or surfactants, which may be selected from the group consisting of non-ionic, anionic, ampholytic and cationic surfactants and mixtures thereof, will normally be present in a high proportion, such as 5-60%, in particular 10-40% by weight, calculated on the composition. The amount of the phenyl carbamate I may be from 1 to 60% by weight, calculated on the composition, and will normally be in the range of 5-40% by weight, calculated on the composition. In addition to the compound I, the oily component and the surfactant, the liquid phase of these concentrated compositions may contain one or several constituents selected from the group consisting of glycols, glycol ethers and combinations thereof, normally in concentrations of 0.1-15%, in particular 2-10%, calculated on the weight of the composition. Furthermore, water in an amount of up to 40% by weight or even more may be incorporated. In practice, it will be considerations concerning the chemical stability of the phenyl carbamate in the individual composition which will dictate the maximum amount of water which can be added. If water is incorporated in the oil/detergent mixture, pH should be controlled into the acidic range, preferably in the optimum range of 2-4, in order to secure optimum chemical stability of the phenyl carbamate.

The oily component and the surfactant may be so selected that they are mutually soluble to form a stable solution which is capable of effectively suspending finely divided phenyl carbamates I and so that the surfactant will effectively emulsify the oil when water is added to form the final preparation ready for use. The surfactant may also contribute to effectively wet the sprayed surface with the preparation. The oily component and the detergent and the relative amounts thereof may also be so selected that they are capable of forming a microemulsion when mixed with an equal amount of water or up to a ten times as high amount of water (a microemulsion is characterized by comprising oil, emulsifier (surfactant) and water in a finely divided state and by being clear and translucent). A microemulsion is stable and cannot normally be separated by centrifugation). The advantage of selecting the oily component and the surfactant in such a manner that they form a microemulsion is, i.a., that the phenyl carbamate I may be added to the oily component/surfactant in wet state, i.e. it is not necessary to completely dry the phenyl carbamate I obtained in the process according to the invention before it is combined with the oily component/surfactant. Another advantage of selecting the oily component and the surfactant in such a manner that they are capable of forming a microemulsion is that the microemulsion, due to its inherent stability, tends to keep the suspension of the phenyl carbamate I stable during transportation and handling of the composition, thus avoiding sedimentation problems. A further advantage connected to compositions in microemulsion form is that the dilution with water for the preparation of solutions ready for use takes place without problems such as lump-forming, etc.

Usable surfactants are non-ionic compounds such as polyethoxylated alkylphenoles, polyethoxylated higher alkanoles, polyethoxylated fatty acids, polyethoxylated amines and amides, monoglycerides and derivatives thereof. Alkylarylsulphonic acids and phosphoric acid esters and salts thereof will also be usable surfactants. Phosphoric acid esters may be mono- and diesters of polyethoxylated higher alkanoles, polyethoxylated alkylphenoles, polyethoxylated distyryl- and tristyrylphenoles and non-ethoxylated alcohols. Furthermore, ampholytes will be usable surfactants. Other surfactants are e.g. as described in McCutcheon's publication: Detergent & Emulsifiers, International Edition, 1983, Glen Rock, N.J. 07452, USA. Corresponding surfactants from other suppliers are, of course, also applicable.

It is believed to be advantageous to use mixtures of ethoxylated surfactants and anionic surfactants, preferably a non-ionic/anionic mixture when the non-ionic components constitute a mixture of surfactants with HLB-values of about 9 (emulsifier) and about 12-13 (wetting agent and dispersing agent), respectively.

In the preparation of the substituted phenyl carbamate composition, the surfactants may be mixed with the oily component yielding a translucent solution. In this solution, coarsely ground dry substituted phenyl carbamate is slurried. The mixture may be ground further, e.g. in a ball mill, yielding at least 99% of the substituted phenyl carbamate with a particle size of less than 10 micron and 50% with a particle size of less than 3-5 micron.

When the substituted phenyl carbamate prepared in aqueous solution is isolated as a wet paste, the content of dry material will normally be about 65-70% after centrifugation. It is possible to use this material slurried in the oil/detergent mixture whereby the water becomes incorporated in the mixture so that the liquid phase comprises a stable microemulsion which can be further ground in the ball mill. In another embodiment, the herbicidally active compound or compounds in the form of an aqueous slurry may be ground to comminute the compound or compounds to a size suitable for being incorporated in the final composition, optionally with addition of a surfactant, whereafter the liquid comprising one or more oily components and one or more surfactants is added. Or the components which when mixed would constitute said liquid are added separately. In either case, the resulting liquid phase will thereby form an emulsion or microemulsion. This is considered to be an advantageous method of utilizing the aqueous slurry obtained in the water phase synthesis described above.

Minor amounts of glycol ethers, e.g. butylglycol, will presumably have an advantageous effect on the viscosity and at the same time offer the possibility of a broader mixture ratio between the microemulsion and water when the composition is to be diluted on the location in which the composition is to be used. Small amounts of water in the composition will often show a viscosity-controlling effect, and glycols such as propylene glycol will stabilize mixtures containing limited amounts of water. The dispersion must show an adequate viscosity. On the one hand, it must be so easy-running that the mixing process with the water used in the dilution proceeds quickly, but on the other hand, it must be sufficiently high-viscous to prevent sedimentation of the active ingredients.

Oil-containing phenmedipham dispersions show a biological effect comparable with preparations made up with isophorone.

Ranges of application of the order of about 0.3 kg of active substance per hectare have been found to be adequate for the selective combating of weeds when two or more applications are performed in the growth season, or when the active substance is sprayed via a band spraying equipment. In other instances, an application rate of about 1 kg of active substance per hectare is normally adequate.

The above-described method for preparing oil-based compositions does not only apply to compositions comprising substituted phenyl carbamates I, but may also be used in the preparation of other compositions comprising other types of herbicides and pesticides. As examples of herbicides may be mentioned 5-amino-4-chloro-2-phenyl-3(2H)pyridazinone (chloridazon), 2-ethoxy-2,3-dihydro-3,3-dimethylbenzofuran-5-yl methanesulphonate (ethofumesate), and 4-amino-4,5-dihydro-3-methyl-6-phenyl-1,2,4-triazin-5-one (metamitron), which may also be used in combination with each other or with the phenyl carbamates I.

Thus, compositions comprising both the phenyl carbamates I and components selected from chloridazon and metamitron are advantageous in that the content of active ingredient may be kept at a lower level as the preferred phenyl carbamates are more active per weight unit than the other herbicidally active components mentioned above.

The above-mentioned compound metamitron is used as a herbicide for beets, normally in a dosis of about 3–4 kg/ha. When metamitron in some cases is preferred instead of phenyl carbamates I which are used in a dosis of about 1 kg/ha only, this is due to the fact that metamitron has a better biological effect against cleavers goosegrass (*Galium aparine*), nippelwort (*Lapsana communis*) and black nightshade (*Solanum nigrum*). A much better biological effect is obtained in the combating of corn marigold (*Chrysanthemum segetum*), wild chamomile (*Matricaria chamomilla*), small nettle (*Urtica urens*) and anual meadow grass (*Poa annua*). The other 15-20 weed species in beets which are common in Denmark are combated equally well with phenmedipham and metamitron.

To this should be added that metamitron in a dosis of 3-4 kg/ha is less aggressive (phytotoxic) to the beet plants than phenmedipham used in a dosis of 1 kg/ha.

Farmers often prefer to use a mixture of metamitron and phenmedipham in which each of the preparations is used in a dosage which is half of the usual dosage. In this way, a biological effect which is fully up to what may be obtained when using metamitron alone is obtained. Nor is the herbicidal mixture more phytotoxic than when metamitron is used alone.

Metamitron is normally commercially available as a 70% wettable powder and phenmedipham as a 16% emulsion composition containing isophorone. Up till now, the farmers have themselves mixed the compositions in connection with the spraying. It is, however, not practical for the user to mix two types of compositions which are so different. The mixing is best performed by diluting each composition separately in part of the dilution water and then performing the mixing. In order to activate the metamitron biologically, mineral oil is often added which oil is emulgated into the spraying solution. Thus, there will be a risk of spraying problems (nozzle stops) if the mixing is not performed carefully. When using several products, there will be a larger risk of wrongly apportioning the products. Finally, when using the present product which is characterized in that both phenmedipham and metamitron are dispersed in an oil/surfactant mixture, it is achieved that the user-contrary to the practice existing up till now-totally avoids dust from the wettable powder, and that isophorone is not used as the solvent.

Thus, an interesting aspect of the invention is a composition comprising phenmedipham or desmedipham in an amount of 2-15%, preferably 3-8%, e.g. about 6% by weight, metamitron in an amount of 5-40%, preferably 10-30%, e.g. about 17% by weight, formulated with an oily component such as mineral oil, e.g. spindle oil, in an amount of 10-75%, e.g. about 30% by weight, a surfactant or surfactant mixture comprising ethoxylated nonyl phenol (3-9ethylene oxide units per molecule) and optionally a phosphoric acid ester salt such as Berol TM 724, monoethanolamine salt, and/or an alkyl or aryl or alkylaryl sulphonic acid salt, such as dodecyl benzene sulphonic acid triethanolamine salt or a linear alkyl ($C_{10}$-$C_{22}$) sulphonic acid salt (LAS), the total amount of surfactant or surfactant mixture being 5-50%, e.g. about 40% by weight, butyl glycol in an amount of 0-10%, e.g. about 7.5% by weight, and optionally water, all amounts calculated on the total composition. A mixed composition may be prepared by mixing a dispersion comprising phenmedipham and a dispersion comprising metamitron, which dispersion may be prepared individually in liquid phases comprising an oily component such as spindle oil in an amount of about 30-35%, a surfactant mixture consisting of an alkyl or aryl or alkylaryl sulphonic acid salt such as dodecyl benzene sulphonic acid-triethanolamine salt in an amount of about 8-10% by weight, ethoxylated nonyl phenol in an amount of about 30-35% by weight and butyl glycol in an amount of about 7-9% by weight.

The solubility of phenmedipham and metamitron in mineral oil is about 0.1%, depending on the content of aromatics in the oil. In the above-described water-emulsifiable liquids which are solutions comprising oil and surfactant, the solubility of phenmedipham and metamitron is about 3% when the content of surfactant in the liquid is of the same order as the content of oil. However, at such a high solubility, there may be a tendency of slow crystal growth of phenmedipham and/or metamitron in the dispersions during storage under varying temperature conditions, which means that the compositions will be less stable under such conditions. In microemulsions with a content of about 25% of water, the solubility of phenmedipham is reduced by a factor of 10 to about 0.3%. A similar reduction does not take place for metamitron. In addition, it tends to be more time-consuming to dilute metamitron dispersions in water than phenmedipham dispersions, probably because of the dissolved proportion of metamitron. However, once emulsions or microemulsions have been formed in the dilution, they are very stable.

To lower the solubility of phenmedipham and metamitron in the liquid and to counteract the tendency for metamitron compositions to be more time-consuming to dilute with water, the proportion of oil in the liquid may be kept high and the proportion of surfactant correspondingly low, and an oil may be used which has a limited content of aromatics, that is, a content of less than 30% by weight, preferably less than 10% by weight. (As an example of a preferred oil for this purpose may be mentioned a mineral oil having a boiling point above 200° C. and a viscosity of less than 100 cSt at 40° C. and, as mentioned above, a content of aromatics of less than 30% by weight, preferably less than 10% by weight.) However, it has been found that if the amount of oil is increased to about 60% and the amount of surfactant is reduced to about 10-15%, there will be a pronounced tendency for the composition to separate sticky sediments of oil and fine-grained herbicide when the composition is diluted with water. Also, the proportion of oil which is emulsified into the water phase will tend to separate again as an upper phase.

Thus, in compositions with a high amount of oil which has a low content of aromatics, there is a pronounced necessity for the use of a highly efficient emulsifier (surfactant) system. A sufficiently efficient emulsifier (surfactant) which will secure a satisfactory emulsifiability of the mineral oils with relatively low content of aromatics may for example be obtained by replacing part of the above-mentioned ethoxylated nonylphenols with ethoxylated dinonylphenols and combining them with either phosphoric acid ester salts such as Berol TM 724 monoethanolamine salt and/or an alkyl or aryl or alkylaryl sulphonic acid ester salt such as dodecyl benzene sulfonic acid triethanolamine salt, the total amount of surfactant being about 5-20%, e.g. about 10-15%, calculated on the composition, and the amount of mineral oil of low aromatics content, e.g. solvent-refined paraffinic mineral oil in an amount of 40-75%, e.g. about 60% by weight. Part of the oil may be replaced with a lower boiling petroleum fraction such as kerosene. Thus, interesting compositions according to the invention comprise 15-40, preferably 20-30% by weight of either phenmedipham or metamitron or a combination of phenmedipham and metamitron dispersed in a liquid phase which contains a mineral oil in an amount of 10-75%, e.g. about 50-70%, such as about 60% by weight, a surfactant or surfactant mixture comprising ethoxylated alkylphenol (containing 3-9 ethylene oxide units) in which the alkyl group contains 4-15, in particular 6-12 carbon atoms, and/or ethoxylated dialkylphenol (containing 4-14 ethylene oxide units) in which the alkyl group contains 4-15, in particular 6-12 carbon atoms, and optionally a phosphoric acid ester salt and/or an alkyl or aryl or alkylaryl sulphonic acid salt, the total amount of surfactant or surfactant mixture being 5–25%, preferably 10–15%, by weight. The mineral oil may, e.g., be solvent-refined mineral oil in an amount of about 50% combined with aromatics-free kerosene (boiling point 190°–240° C.) in an amount of about 10%, the ethoxylated dinonylphenol (containing 9 ethylene oxide units) may, e.g., be present in an amount of about 5%, the ethoxylated nonylphenol (containing 4 ethylene oxide units) may, e.g., be present in an amount of about 3% and phosphoric acid ester (Berol TM 724) monoethanolamine salt may, e.g., be present in an amount of about 5%. The amount of dispersed phenmedipham should preferably constitute 20–40%, more preferably 25–35% of the composition, and the amount of dispersed metamitron should preferably constitute 15–35%, more preferably 20–30% of the composition. Combined compositions may be prepared by mixing phenmedipham and metamitron dispersions. The dispersions prepared in this manner are easy to dilute with water. Both phenmedipham and metamitron are dispersed satisfactorily, and the oily phase forms sufficiently stable emulsions in the water. In these oil-detergent mixtures, the solubility of phenmedipham and metamitron is about 0.2%. The compositions are preferably substantially free from water which increases the chemical stability of the active substances.

EXAMPLE 1

Preparation of methyl N-(3-hydroxyphenyl)carbamate

3-Aminophenol (10.9 g, 0.10 mole) in water (100 ml) was placed in a 250 ml beaker equipped with a stirrer, a thermometer and a pH electrode. The suspension was stirred and cooled to 10° C. by external cooling.

By means of a separatory funnel methyl chloroformate (9.45 g, 0.10 mole) was added to the suspension over a period of 1 hour with continuous stirring, and the temperature was maintained at 8°–12° C. During the addition of the ester, the pH was adjusted to 5.3 by simultaneous addition of a 50% NaOH solution.

After the addition of the ester, the stirring and the pH adjusting was continued for ½ hour while the temperature was allowed to increase to room temperature. Subsequently, the pH was lowered to 1.9 with 4N HCl for ¼ hour to dissolve unreacted 3-aminophenol as its hydrochloride.

The product, which was a fine, suspended powder, was filtered, washed with icewater (2×25 ml) and dried to yield methyl N-(3-hydroxyphenyl)carbamate (15.0 g, 90%), m.p. 94°–95° C. Titration of the hydroxy group with 0.5N NaOH showed a purity of 98%.

EXAMPLE 2

Preparation of methyl N-(3-hydroxyphenyl)carbamate

3-Aminophenol (27.3 g, 0.25 mole) in water (250 ml) was placed in a 500 ml beaker equipped with a stirrer, a thermometer and a pH electrode. The suspension was stirred and cooled to 20° C. by external cooling.

By means of a separatory funnel methyl chloroformate (23.6 g, 0.25 mole) was added to the suspension over a period of 1 hour with continuous stirring, and the temperature was maintained at 20° C. During the addition of the ester, the pH was adjusted to 5.3 by simultaneous addition of a 50% NaOH solution.

After the addition of the ester, the stirring and the pH adjusting was continued for ½ hour while the temperature was allowed to increase to room temperature. Subsequently, the pH was lowered to 1.9 with 4N HCl for ¼ hour to dissolve unreacted 3-aminophenol as its hydrochloride.

The product, which was a fine, suspended powder, was filtered, washed with icewater (2×50 ml) and dried to yield methyl N-(3-hydroxyphenyl)carbamate (36.4 g, 87.2%), m.p. 96.0°–96.5° C. Titration of the hydroxy group with 0.5N NaOH showed a purity of 99.4%.

EXAMPLE 3

Preparation of methyl (3-(3-tolyl-carbamoyloxy)phenyl)carbamate

Methyl N-(3-hydroxyphenyl)carbamate (8.35 g, 0.05 mole) (prepared as described in Example 1) in water (75 ml) was placed in a 150 ml beaker equipped with a stirrer, and the mixture was stirred. Triethylamine (0.25 ml) was added, and over a period of ¾ hour 3-tolyl isocyanate (6.65 g, 0.05 mole) was added by means of a separatory funnel without any adjustment of temperature or pH.

After the addition of the 3-tolyl isocyanate, the stirring was continued for 1 hour. Subsequently the product, which was a very fine, suspended powder, was filtered and dried to yield the title product (13.9 g, 93%), m.p. 139°–143° C.

HPLC-Analysis showed a purity of 95%, the remaining 5% being methyl N-(3-hydroxyphenyl)carbamate and a by-product, N,N'-di-3-tolylurea.

EXAMPLE 4

Preparation of methyl (3-(3-tolyl-carbamoyloxy)phenyl)carbamate

Methyl N-(3-hydroxyphenyl)carbamate (83.5 g, 0.50 mole) (prepared as described in Example 1) in water (500 ml) was placed in a 1 l beaker equipped with a stirrer, and the mixture was stirred and cooled to 10° C. Triethylamine (2.5 ml) was added, and over a period of ½ hour 3-tolyl isocyanate (66.5 g, 0.50 mole) was added by means of a separatory funnel without any adjustment of pH, while the temperature was maintained at 10° C.

After the addition of the 3-tolyl isocyanate, the stirring was continued for 1 hour. Subsequently the product, which was a very fine, suspended powder, was filtered and dried to yield the title product (147.9 g, 98.6%), m.p. 141°–144° C.

HPLC-Analysis showed a purity of 96.1%, the remaining 3.9% being methyl N-(3-hydroxyphenyl)carbamate and a by-product, N,N'-di-3-tolylurea.

EXAMPLE 5

Preparation of methyl (3-(3-tolyl-carbamoyloxy)phenyl)carbamate

Methyl N-(3-hydroxyphenyl)carbamate (8.35 g, 0.05 mole) (prepared as described in Example 1) in water (75 ml) was placed in a 150 ml beaker equipped with a stirrer, and the mixture was stirred. Over a period of ¾ hour 3-tolyl isocyanate (6.65 g, 0.05 mole) was added by means of a separatory funnel without any adjustment of temperature. During the addition pH was maintained at 9.5 by simultaneous addition of 50% NaOH solution.

After the addition of the 3-tolyl isocyanate, the stirring was continued for 1 hour. Subsequently the product, which was a very fine, suspended powder, was filtered and dried to yield the title product (14.0 g, 93.3%), m.p. 139°–143° C. HPLC-Analysis showed a purity of 94.1%, the remaining 5.9% being methyl N-(3- hydroxyphenyl)carbamate and a by-product, N,N'-di-3-tolylurea.

EXAMPLE 6

Preparation of methyl (3-(3-tolyl-carbamoyloxy)phenyl)carbamate

Methyl N-(3-hydroxyphenyl)carbamate (8.35 g, 0.05 mole) (prepared as described in Example 1) in water (75 ml) was placed in a 150 ml beaker equipped with a stirrer, and the mixture was stirred. Borax (2.0 g) was added, and over a period of ¾ hour 3-tolyl isocyanate (5.3 g, 0.04 mole) was added by means of a separatory funnel without any adjustment of temperature. The pH value was 9.2 during the reaction time.

After the addition of the 3-tolyl isocyanate, the stirring was continued for 1 hour. Subsequently the product, which was a very fine, suspended powder, was filtered, washed and dried to yield the title product (12.0 g, 100% calculated on the isocyanate intermediate), m.p. 139.8°–141.8° C.

HPLC-Analysis showed a purity of 95.2%, the remaining 4.8% being methyl N-(3-hydroxyphenyl)carbamate and a by-product, N,N'-di-3-tolylurea.

EXAMPLE 7

Preparation of methyl (3-(3-tolyl-carbamoyloxy)phenyl)carbamate

3-Aminophenol in water (1 mole/l) was placed in a reaction vessel equipped with a stirrer, a thermometer and a pH electrode. The suspension was stirred and cooled to 10° C. by addition of ice. The pH in the suspension was adjusted to 5.3 by initial addition of HCl.

By means of a separatory funnel methyl chloroformate (in stoichiometric amount) was added to the suspension over a period of 1 hour with continued stirring, and the temperature was maintained below 10° C. During the addition of the ester, the pH was maintained at 5.3 by simultaneous addition of a 50% NaOH solution.

After the addition of the ester, the stirring and the pH adjusting was continued for ½ hour whereafter pH was raised to 9.2. After the addition of water (so that the concentration was 0.5 mole/l), borax and a small amount of the title product (seed) 3-tolyl isocyanate (in stoichiometric amount) was added by means of a separatory funnel without any adjustment of temperature. The pH value was 9.2 during the reaction time.

After the addition of the 3-tolyl isocyanate, the stirring was continued for 1 hour. Subsequently the product, which was a very fine, suspended powder, was filtered, washed and dried to yield the title product in 100% yield, m.p. 140°–142° C.

HPLC-Analysis showed a purity of 95%.

EXAMPLE 8

Solvent extraction of methyl (3-(3-tolylcarbamoyloxy)phenyl)carbamate 1 liter of a reaction mixture containing about 88 g of methyl (3-(3-tolylcarbamoyloxy)phenyl)carbamate was prepared as described in Example 7, but the powder was not filtered off. Analysis of the end product formed showed a purity of 94%.

The pH in the reaction mixture was adjusted to 2 by addition of hydrochloric acid, and sodium chloride (100 g) was dissolved in the slurry. Isophorone (300 g) was added with stirring and the stirring was continued until the solid has dissolved.

The isophorone phase was separated and dried by means of sodium sulfate. The sodium sulfate was filtered off and acetic acid anhydride (5.0 g) was added.

Analysis showed a content of 21.6% of methyl (3-(3-tolylcarbamoyloxy)phenyl)carbamate.

EXAMPLE 9

Stability tests

A solution of methyl (3-/3-tolylcarbamoyloxy)-phenyl)carbamate in isophorone was prepared as described in Example 8 and divided into 4 equal parts. The samples were subjected to storage tests as described in the table below, with or without addition of acetic acid anhydride, optionally after drying with sodium sulfate. The tests were performed after 24 hours/25° C., 26 days/25° C., and 25 days/70° C., respectively.

TABLE

| Drying and/or stablizing agent added | Active ingredient, % by weight | | |
|---|---|---|---|
| | 24 hours/ 25° C. | 26 days/25° C. | 25 days/70° C. |
| — | 20.68 | 20.93 | 20.56 |
| 1.0 g AAA/50 ml | 21.32 | 20.44 | 19.76 |
| Na$_2$SO$_4$ | 20.79 | 20.94 | 20.67 |
| Na$_2$SO$_4$ + 1.0 g AAA/50 ml | 21.56 | 20.43 | 19.69 |

AAA = acetic acid anhydride

EXAMPLE 10

Preparation of ethyl N-(3-hydroxyphenyl)carbamate

3-Aminophenol (10.9 g, 0.10 mole) in water (100 ml) was placed in a 250 ml beaker equipped with a stirrer, a thermometer and a pH electrode. The suspension was stirred and cooled to 10° C. by external cooling.

By means of a separatory funnel ethyl chloroformate (10.85 g, 0.10 mole) was added to the suspension over a period of 1 hour with continuous stirring, and the temperature was maintained at 8°–12° C. During the addition of the ester, the pH was adjusted to 5.3 by simultaneous addition of a 50% NaOH solution.

After the addition of the ester, the stirring and the pH adjusting was continued for ½ hour while the temperature was allowed to increase to room temperature. Subsequently, the pH was lowered to 1.9 with 4N HCl for ¼ hour to dissolve unreacted m-aminophenol as its hydrochloride.

The product, which was a fine, suspended powder, was filtered, washed with icewater (2×25 ml) and dried to yield ethyl N-(3-hydroxyphenyl)carbamate (16.7 g, 92%), m.p. 98.0°–99.5° C. Titration of the hydroxy group with 0.5N NaOH showed a purity of 98%.

EXAMPLE 11

Preparation of ethyl (3-phenyl-carbamoyloxyphenyl)carbamate

Ethyl N-(3-hydroxyphenyl)carbamate (18.1 g, 0.10 mole) (prepared as described in Example 8) in water (100 ml) was placed in a 250 ml beaker equipped with a stirrer, and the mixture was stirred. Borax (1.0 g) was added, and over a period of ¾ hour phenyl isocyanate (11.9 g, 0.10 mole) was added by means of a separatory funnel without any adjustment of temperature. The pH value was 9.2 during the reaction time.

After the addition of the phenyl isocyanate, the stirring was continued for 1 hour. Subsequently the product, which was a very fine, suspended powder, was filtered, washed and dried to yield the title product (29.1 g, 96.9%).

EXAMPLE 12

Preparation of methyl (3-(3-tolyl-carbamoyloxy)phenyl)carbamate

Methyl N-(3-hydroxyphenyl)carbamate (14 g, 0.084 moles) (prepared as described in Example 1) in water (300 ml) was placed in a 500 ml beaker equipped with a stirrer and a pH-electrode, pH was adjusted to 9.2, and the temperature was 25° C. Over a period of 2 hours, 3-tolyl carbamic acid chloride (14 g, 0.083 moles) in acetone (100 ml) was added by means of a separatory funnel. During the addition, pH was maintained at 9.2 by simultaneous addition of 50% NaOH solution.

After the addition of 3-tolyl carbamic acid chloride, the stirring was continued for 15 minutes. Subsequently, the reaction mixture was acidified, and the product which was a very fine, suspended powder was filtered, washed and dried to yield the title product (22 g, 92%).

The purity of the product was not as good as when prepared with 3-tolyl isocyanate, but the reaction proceeded smoothly.

The 3-tolyl carbamic acid chloride was prepared by bubbling dry HCl through a solution of 3-tolyl isocyanate in petroleum ether from which the product precipitated.

EXAMPLE 13

Concentrated solution of phenmedipham in isophorone with ampholyte

| | |
|---|---|
| Methyl (3-(3-tolyl-carbamoyloxy)phenyl)-carbamate (Tech. grade) | 165 g |
| Isophorone | 605 g |
| Xylene | 50 g |
| Maleic anhydride | 30 g |
| Salicylic acid | 10 g |
| Ethoxylated castor oil, HLB about 13.5 | 90 g |
| Coco-alkyl-β-amino propionic acid | 50 g |
| Total | 1000 g |

The carbamate was dissolved in isophorone and xylene and the remaining components were added.

EXAMPLE 14

Concentrated solution of phenmedipham in isophorone with ampholyte

| | |
|---|---|
| Methyl (3-(3-tolyl-carbamoyloxy)phenyl)-carbamate (Tech. grade) | 165 g |
| Isophorone | 583 g |
| Xylene | 50 g |
| Di-isobutyl succinate | 50 g |
| Nitric acid, 65%, ad pH 2.5-3.0 | 12 g |
| Ethoxylated nonylphenol (HLB 13) | 90 g |
| Coco-alkyl-β-amino propionic acid | 50 g |
| Total | 1000 g |

The carbamate was dissolved in isophorone and xylene and the remaining components were added.

EXAMPLE 15

Phenmedipham dispersions comprising an oil-based microemulsion or solution as the liquid phase Microemulsions I and III and a solution II were prepared without phenmedipham by mixing the constituents. Then, one part by weight of phenmedipham (technical grade, 96%) was incorporated into 3 parts by weight of the liquid phase in each of I, II and III, and each of the resulting mixtures was ground in a ball mill charged with glass balls (φ1 mm).

Turbidity temperatures for the microemulsions I and III and the solution II and the appearance of microemulsions formed therefrom upon addition of tap water are stated in Table 1. It will be noted that they all appear as homogeneous liquids which do not separate into their components.

After standing for 3 weeks at 45°-50° C., all of the phenmedipham-containing dispersions were uniform after moderate shaking.

TABLE 1

| | I | II | III |
|---|---|---|---|
| Water | 25.9% | | 21.0% |
| Monoethanolamine | 2.6% | | |
| Berol TM 724 1) | 10.3% | | |
| Triethanolamine | | 2.5% | 2.0% |
| Sulfosoft TM 2) | | 5.7% | 4.5% |
| Spindle oil 5) | 17.2% | 28.4% | 18.2% |
| Marlophen TM 88 H 3) | 12.1% | 18.5% | 12.8% |
| Berol TM 26 4) | 5.2% | 12.8% | 8.2% |
| Butyl glycol | 1.7% | 7.1% | 4.6% |
| Propylene glycol | | | 3.7% |
| Total | 75.0% | 75.0% | 75.0% |
| Appearance | translucent yellow liquid | translucent yellowish brown liquid | translucent yellow liquid |
| pH (in a 1:10 dilution with water) | 2.8 | 3.4 | 3.7 |
| Turbidity temp. | 60° C. | >80° C. | 58° C. |
| Dilution 1:1 | Translucent yellow liquid | Translucent yellow liquid | Translucent yellow liquid |
| Dilution 1:1, after 24 h | Slightly turbid liquid | Translucent gelatinous liquid | Translucent liquid |
| Dilution 1:10 | Translucent slightly opaque liquid | Translucent liquid | Translucent liquid |
| Dilution 1:50 | Translucent liquid | Opaque, but translucent liquid | Translucent slightly opaque liquid |
| Technical grade phenmedipham, 96% | 25% | 25% | 25% |
| % of phenmedipham in composition | 24% | 24% | 24% |

1) Acidic phosphoric acid ester (Berol Kemi)
2) Dodecylbenzenesulfonic acid (Berol Kemi)
3) Ethoxylated nonylphenol (8 ethylene oxide units per molecule) (Hüuls)
4) Ethoxylated nonylphenol (4 ethylene oxide units per molecule) (Berol Kemi)
5) Gravex TM (Shell)

EXAMPLE 16

Phenmedipham and metamitron dispersions comprising an oil-based solution as the liquid phase Dispersions I and II with the contents as stated below were prepared in the same manner as described in Example 15.

| Ingredients | Dispersion I | Dispersion II |
|---|---|---|
| Triethanolamine | 2.6% | 2.5% |
| Sulfosoft TM | 5.9% | 5.7% |
| Spindle oil | 29.3% | 28.4% |
| Marlophen TM 88H | 19.1% | 18.5% |
| Berol TM 26 | 13.2% | 12.8% |
| Butyl glycol | 7.4% | 7.1% |
| | 77.5% | 75.0% |
| Metamitron, Tech. grade, 98% | 22.5% | |

| Ingredients | Dispersion I | Dispersion II |
|---|---|---|
| Phenmedipham, Tech. grade, 96% | | 25.0% |
| pH of dispersion (in a 1:10 dilution with water) | 3–4 | 3–4 |

A combined composition consisting of 75% by weight of dispersion I and 25% by weight of dispersion II was prepared by mixing the dispersions. The composition formed was a viscous composition containing about 6% of phenmedipham and about 17% of metamitron which could be diluted with water by somewhat prolonged mixing and resulted in stable dispersions.

EXAMPLE 17

Metamitron dispersion comprising an oil-based solutio as the liquid phase

Solutions I and II were prepared by mixing, and one part by weight of metamitron (technical grade, 98%) was incorporated into 3 parts by weight of the liquid phase in each of I and II, and each of the resulting mixtures was ground in a ball mill charged with glass balls ($\phi$1 mm).

Turbidity temperatures for the resulting solutions I and II and the appearance of the microemulsions formed upon addition of tap water to the solutions are stated in Table 2. It will be noted that they all appear as homogeneous liquids which do not separate into their components.

TABLE 2

| | I | II |
|---|---|---|
| Monoethanolamine | 2.9% | 2.7% |
| Berol TM 724 1) | 12.6% | 13.5% |
| Spindle oil 5) | 33.6% | 32.4% |
| Solvesso TM 150* | 3.5% | 3.4% |
| Marlophen TM 88 H 3) | 14.0% | 13.5% |
| Berol TM 26 4) | 8.4% | 8.1% |
| 60% solution of cocoalkyl $\beta$-aminopropionic acid in diethyleneglycol | 0.0% | 1.4% |
| Total | 75.0% | 75.0% |
| Appearance | translucent yellow liquid | translucent yellow liquid |
| pH (in a 1:10 dilution with water) | about 3 | about 3 |
| Turbidity temp. | 45° C. | 44° C. |
| Dilution 1:1 | Translucent yellow liquid | Slightly turbid liquid |
| Dilution 1:10 | Translucent liquid | Opague, but translucent liquid |
| Dilution 1:50 | Translucent liquid | Translucent liquid |
| Technical grade metamitron, 98% | 25% | 25% |

*Solvesso TM 150 is a 99% aromatic hydrocarbon, flash point 166° C., boiling point 187–210° C., available from Exxon Corporation.

EXAMPLE 18

Metamitron and phenmedipham dispersions comprising an oil-based solution as the liquid phase Dispersions I and II with the contents as stated in Table 3 were prepared in the same manner as described in Example 15.

TABLE 3

| | I | II |
|---|---|---|
| Hydro Para 19 6) | 51.2 | 47.7 |
| Halpasol TM 190/240 7) | 10.2 | 9.5 |
| Berol TM 26 4) | 3.1 | 2.9 |
| Berol TM 269 8) | 5.1 | 4.8 |
| Berol TM 724 1) | 4.4 | 4.1 |
| Monoethanolamine | 1.0 | 1.0 |
| | 75.0% | 70.0% |
| Technical grade phenmedipham, 96% | | 30.0% |
| Technical grade metamitron, 98% | 25.0% | |
| % of phenmedipham in composition | | 28.8% |
| % of metamitron in composition | 24.5% | |
| pH (in a 1:10 dilution with water) | about 3 | about 3 |

1) Acidic phosphoric acid ester (Berol Kemi)
4) Ethoxylated nonylphenol (4 ethylene oxide units per molecule) (Berol Kemi)
6) Solvent refined paraffinic mineral oil (Norsk Hydro) (4% aromatics, viscosity 19.7 cSt at 40° C.)
7) Paraffin hydrocarbon, <0.1% of aromatic hydrocarbon, boiling point 190–240° C., flash point >70° C. (Haltermann)
8) Ethoxylated dinonylphenol (9 ethylene oxide units per molecule) (Berol Kemi)

When mixed with water, the oil-containing liquid phases do not form stable transparent microemulsions as described in the preceding examples, but rather form conventional emulsions which, however, precipitate oil only very slowly. The tendency to separate sediments of oil which contain fine-grained metamitron or phenmedipham, respectively, is negligible.

A combined composition of 77.5% by weight of dispersion I and 22.5% by weight of dispersion II was prepared by mixing the dispersions. The composition contained about 19% of metamitron and 6.5% of phenmedipham.

Dispersion I (metamitron) and the mixed dispersion mentioned above are both thixotropic. Although they seem somewhat viscous, they are easily mixed (emulsified and dispersed) in 98–95% of water. The mixing is made easier because the density of the dispersions are less than that of water.

I claim:

1. A stabilized liquid herbicidal composition comprising at least one of phenmedipham (methyl (3-(3-tolylcarbamoyloxy)phenyl)carbamate) and desmedipham (ethyl 3-phenyl-carbamoyloxyphenyl)carbamate) in an amount of 1–60% by weight in finely ground state and dispersed in a liquid phase which comprises one or more oily components selected from the group consisting of mineral oils and vegetable oils, which are liquid at normal temperatures, are immiscible with water in a ratio of 1:10–10:1, and in which the solubility of phenmedipham or desmedipham is less than 1% by weight, said oily component constitutes 5–75% by weight, one or more surfactants in an amount of 5–60% by weight and optionally water, and which liquid phase is able to form an oil-in-water emulsion or a microemulsion when mixed with up to ten volumes of water.

2. A composition according to claim 1 in which the oil is a mineral oil having a boiling point above 200° C. and a viscosity of less than 100 cSt at 40° C.

3. A composition according to claim 2 in which the oil has a content of aromatics of less than 30% by weight, preferably less than 10% by weight.

4. A composition according to claim 1 wherein the oily component constitutes 15–65% by weight of the composition.

5. A composition according to claim 1 wherein the surfactant(s) is/are selected from the group consisting of non-ionic, anionic, ampholytic and cationic surfactants and mixtures thereof.

6. A composition according to claim 5 wherein the surfactant constitutes 10–40% by weight of the composition.

7. A composition according to claim 1 wherein the herbicidally active compound constitutes 5–40% by weight of the composition.

8. A composition according to claim 1 in which the liquid phase contains one or more constituents selected from the group consisting of water, glycols, glycol ethers and combinations thereof dissolved or homogeneously distributed in the liquid phase.

9. A composition according to claim 1 in which the oily component and the surfactant and the relative amounts thereof are adapted such that the liquid phase forms a microemulsion or a translucent emulsion when mixed with water in the ratio of 1:1–1:10 by weight.

10. A composition according to claim 1 which comprises 15–40% by weight of either phenmedipham or a combination of phenmedipham and metamitron dispersed in a liquid phase which contains a mineral oil in an amount of 10–75% by weight, a surfactant or surfactant mixture comprising ethoxylated alkylphenol containing 3–9 ethylene oxide groups and/or ethoxylated dialkylphenol containing 4–14 ethylene oxide groups and optionally a phosphoric acid ester salt and/or an alkyl or aryl or alkylaryl sulphonic acid salt, the total amount of surfactant or surfactant mixture being 5–25% by weight.

11. A composition according to claim 1 which comprises 20–30% by weight of either phenmedipham or a combination of phenmedipham and metamitron dispersed in a liquid phase which contains a mineral oil in an amount of about 50–70% by weight, a surfactant or a surfactant mixture comprising ethoxylated alkylphenol containing 3–9 ethylene oxide groups and/or ethoxylated dialkylphenol containing 4–14 ethylene oxide groups and optionally a phosphoric acid ester salt and/or an alkyl or aryl or alkylaryl sulfonic acid salt, the total amount of surfactant or surfactant mixture being 10–15% by weight.

12. A composition according to claim 9 which comprises phenmedipham in an amount of about 2–15% by weight, and metamitron in an amount of about 5–40% by weight.

13. A composition according to claim 9 which comprises phenmedipham in an amount of about 6% by weight and metamitron in an amount of about 15–20% by weight.

14. A composition according to claim 1 in which the amount of water present in the composition is up to 40% by weight.

15. A composition according to claim 14, wherein the liquid phase is acidic.

* * * * *